United States Patent [19]
Smith et al.

[11] Patent Number: 5,932,414
[45] Date of Patent: *Aug. 3, 1999

[54] METHODS AND COMPOSITIONS FOR THE MONITORING AND QUANTITATION OF MINIMAL RESIDUAL DISEASE IN HEMATOPOIETIC TUMORS

[75] Inventors: R. Graham Smith; Richard J. Baer, both of Dallas, Tex.

[73] Assignee: University of Texas Systems Board of Regents, Austin, Tex.

[ * ] Notice: This patent is subject to a terminal disclaimer.

[21] Appl. No.: 08/405,373

[22] Filed: Mar. 15, 1995

Related U.S. Application Data

[63] Continuation of application No. 07/621,140, Nov. 28, 1990, abandoned, which is a continuation-in-part of application No. 07/613,197, Nov. 14, 1990, abandoned, which is a continuation-in-part of application No. 07/590,408, Sep. 28, 1990, abandoned.

[51] Int. Cl.$^6$ .............................. C12Q 1/68; C07H 21/04
[52] U.S. Cl. ........................ 435/6; 536/24.3; 536/24.31; 536/24.33
[58] Field of Search .............................. 435/6, 7.92, 91.1, 435/91.2, 91.5; 536/23.1, 24.3, 24.31, 24.33

[56] References Cited

U.S. PATENT DOCUMENTS 4,683,202  7/1987  Mullis .................................. 435/91.2

OTHER PUBLICATIONS

Chen et al., EMBO, vol. 9, No. 2, pp. 415–424, 1990.
Finger et al., PNAS, vol. 86, pp. 5039–5043, Jul. 1989.
Gabert et al., Tl Lancet, 11 Nov., 1989, pp. 1125–1127.

*Primary Examiner*—David Guzo
*Attorney, Agent, or Firm*—Jenkens & Gilchrist, P.C.

[57] ABSTRACT

Methods and compositions for monitoring the presence of minimal residual hematopoietic tumor cells, such as T-cell acute lymphoblastic leukemia cells, in remission cells of a patient. The invention relates to using nucleic acid hybridization probes to detect alteration of tal-1 locus on chromosome 1 from a DNA extract to confirm the presence of residual T-cell acute lymphoblastic leukemia cells in the patient. Methods to quantitate the amount of hematopoietic cells are described. Kits for detecting and monitoring hematopoietic tumor cells in a patient are provided. Kits for quantitating hematopoietic tumor cells in a patient in remission are also provided.

23 Claims, 7 Drawing Sheets

|                      |                                              |           |           |        |
|----------------------|----------------------------------------------|-----------|-----------|--------|
| germline centrmeric 1p | CATTCCTCACAATTTCTGGCTCACACTCTGCTACGTAGTAAGGG |           |           | SEQ. ID NO.1 |
| Cell line RPMI 8402  | CATTCCTCACAATTTC                             | cggatcaaa | TCATTTCTTC | 159 bp | SEQ. ID NO.2 |
| MOLT 16              | CATTCCTCACAATTTCTGGCTCTA                     | ttaggggttc | GGTTTTCATTTCTTC | 172 bp | SEQ. ID NO.3 |
| Patient L14          | CATTCCTCACAATTTCTGG                          | gaaacgactt | TTGGTTTTCATTTCTTC | 170 bp | SEQ. ID NO.4 |
| L54                  | CATTCCTCACAATTTCTGGC                         |           | GTTGGTTTTCATTTCTTC | 162 bp | SEQ. ID NO.5 |
| L81                  | CATTCCTCACAATTTCTGG                          | g         | GGTTTTCATTTCTTC | 159 bp | SEQ. ID NO.6 |
| germline telomeric 1p |                                             | AAATGCGCCAGGCTGTGGTTGGTTTTCATTTCTTC |           |        | SEQ. ID NO.7 |

*FIG. 1B*

METHODS AND COMPOSITIONS FOR THE MONITORING AND QUANTITATION OF MINIMAL RESIDUAL DISEASE IN HEMATOPOIETIC TUMORS

This is a continuation of application Ser. No. 07/621,140, filed on Nov. 28, 1990, which was abandoned upon the filing hereof, which is a continuation-in-part of Ser. No. 07/613,197, filed Nov. 14, 1990, now abandoned, which is a continuation-in-part of Ser. No. 07/590,408, filed Sep. 28, 1990, now abandoned.

The U.S. Government may own certain rights in the present invention pursuant to NIH Grant Numbers CA 42891, CA 44016, CA 46593, and CA 47975.

FIELD OF THE INVENTION

The present invention relates to methods and compositions for detecting, monitoring and quantitating minimal residual disease in hematopoietic tumors in a human, and in particular, relates to using oligonucleotide probes to monitor residual T-cell acute lymphoblastic leukemia in the blood, bone marrow and other body fluids from patients who are being treated for this leukemia.

BACKGROUND OF THE INVENTION

T-cell acute lymphoblastic leukemia (T-ALL) comprises about 15% of all cases of acute lymphoblastic leukemia (ALL). Features that distinguish this disease from B-lineage ALL include higher incidence in males, older mean age at diagnosis, high mean blood leukocyte count and the frequent presence of a mediastinal mass (Sen, L., and L. Borella (1975) "Clinical importance of lymphoblasts with T-markers in childhood leukemia," *N. Engl. J. Med.* 292:828–832; Tsukimoto, I., et al. (1976) "Surface markers and prognostic factors in acute lymphoblastic leukemia," *N. Engl. J. Med.* 294:245–248; Roper, M., et al. (1983) "Monoclonal antibody characterization of surface antigens in childhood T-cell lymphoid malignancies," *Blood* 61:830–837). Although significant improvements in long-term disease-free survival for both children (Shuster, J. J., et al. (1990) "Prognostic factors in childhood T-cell acute lymphoblastic leukemia: a Pediatric Oncology Group study," *Blood* 75:166–173; Pui, C. H., et al. (1990) "Heterogeneity of presenting features and their relation to treatment outcome in 120 children with T-cell acute lymphoblastic leukemia," *Blood* 75:174–179.) and adults (Hoelzer, D., et al. (1988) "Prognostic factors in a multicenter study for treatment of acute lymphoblastic leukemia in adults," *Blood* 71:123–131; Gaynor, J., et al. (1988) "A cause-specific hazard rate analysis of prognostic factors among 199 adults with acute lymphoblastic leukemia: The Memorial Hospital experience since 1969," *J. Clin. Oncol.* 6:1014–1030) have resulted from contemporary therapeutic programs, about 40% of children and at least 60% of adults with T-ALL still relapse and die of drug-resistant disease. Such failure is presumably due to residual leukemic cells which resist standard therapy. Therefore, a major challenge is to improve the detection and monitoring of minimal residual disease in patients receiving treatment. A sensitive and specific assay for residual leukemia is needed to direct the development of strategies for prevention of disease recurrence.

Since induction of complete remission is achieved in the vast majority of patients, current efforts to prevent treatment failure focus upon modifications of post-remission consolidation and/or maintenance chemotherapy. Unfortunately, the disease is not detectable by routine analysis during the remission period; thus, the effect of therapy on tumor burden is difficult to assess. A sensitive clonal assay for the residual leukemic population during remission would help guide therapeutic decisions beyond the induction period.

A number of chromosomal translocations are associated with T-ALL (Raimondi, S. C., et al. (1988) "Cytogenetics of childhood T-cell leukemia," *Blood* 72:1560–1566; Kaneko, Y., et al. (1989) "Chromosomal and immunophenotypic patterns in T cell acute lymphoblastic leukemia (T ALL) and lymphoblastic lymphoma (LBL)," *Leukemia* 3:886–892; Ucken, F. M., et al. (1989) "Immunophenotype-karyotype associations in human acute lymphoblastic leukemia," *Blood* 73:271–280). Theoretically, the underlying molecular rearrangements could form the basis for sensitive clonal assays for minimal residual disease (Delfau, M. H., et al. (1990) "Detection of minimal residual disease in chronic myeloid leukemia patients after bone marrow transplantation by polymerase chain reaction," *Leukemia* 4:1–5; Snyder, D. S., et al. (1989) "Definition of remission based on the expression of bcr-abl RNA following bone marrow transplant for chronic myelogenous leukemia in chronic phase," *Blood* 74 (Supl. 1):29a (Abstr.); Kohler, S., et al. (1989) "Application of the polymerase chain reaction to the detection of minimal residual disease after bone marrow transplantation for patients with chronic myelogenous leukemia," *Blood* 74 (Supl. 1):29a (Abstr.)). However, no single translocation is found in more than 5–10% of cases, and 20–30% of these leukemias display no karyotypic abnormalities at all (Raimondi, S. C., et al. (1988) "Cytogenetics of childhood T-cell leukemia," *Blood* 72:1560–1566; Kaneko, Y., et al. (1989) "Chromosomal and immunophenotypic patterns in T cell acute lymphoblastic leukemia (T ALL) and lymphoblastic lymphoma (LBL)," *Leukemia* 3:886–892; Ucken, F. M., et al. (1989) "Immunophenotype-karyotype associations in human acute lymphoblastic leukemia," *Blood* 73:271–280). This cytogenetic heterogeneity suggests that a number of loci will need to be characterized in detail before specific molecular probes suitable for detection of occult leukemia in the majority of cases can be prepared.

Chromosome 1 harbors a genetic locus (designated tal, for T-cell acute leukemia) involved in leukemogenesis. The tal-1 gene was identified upon analysis of t(1:14)(p34;q11). Recently, the breakpoint regions derived from one recurrent cytogenetic defect in T-ALL, namely the t(1;14)(p34;q11) translocation were isolated and sequenced (Chen, Q., et al. (1990) "The tal gene undergoes chromosome translocation in T cell leukemia and potentially encodes a helix-loop-helix protein," *EMBO J.* 9:415–424; Chen, Q., et al. (1990) "Coding sequences of the tal-1 gene are disrupted by chromosome translocation in human T cell leukemia," *J. Exp. Med.* 172:1403–1408). In 6 cases analyzed in detail, the breakpoints on chromosome 1 clustered within a 1 kb region. This translocation cleaves the tal-1 gene on chromosome 1, separating its 5' end from the rest of the gene which is transposed into the T cell receptor α/γ locus on chromosome 14. The tal-1 gene potentially encodes a protein containing a helix-loop-helix domain, which is found in a growing number of highly conserved DNA binding proteins involved in the regulation of growth and development (Murre, C., et al. (1989) "A new DNA binding and dimerization motif in immunoglobulin enhancer binding, daughterless, MyoD, and myc proteins," *Cell* 56:777–783). Several genes in this family are known to be disrupted in subsets of ALL (Leder, P., et al. (1983) "Translocations among antibody genes in human cancer," *Science* 222:765–771; Mellentin, J. D., et al. (1989) "lyl-1, a novel gene altered by chromosomal translocation in T cell leukemia, codes for a protein with a helix-loop-helix DNA binding motif," *Cell* 58:77–83; Mellentin, J. D., et al. (1989) "The gene for enhancer binding proteins E12/E47 lies at the t(1;19) breakpoint in acute leukemias," *Science* 246:379–382; Nourse, J., et al. (1990) "Chromosomal translocation t(1;19) results in synthesis of a homeobox fusion mRNA that codes for a potential chimeric transcription factor," *Cell* 60:535–545; Kamps, M. P., et al. (1990) "A new homeobox gene contributes the DNA binding domain of the t(1;19) translocation protein in pre-B ALL," *Cell* 60:547–555). Although of potential pathogenic significance, the t(1;14)(p34;q11) translocation is found in only 3% of T-ALLs (Carroll, A., et al. (1990) "The t(1;14)(p34;q11) translocation is non-random and restricted to T-cell acute lymphoblastic leukemia," *Blood* 76:1220–1224).

To investigate the possibility of a wider role for the tal-1 gene in T-ALL, rearrangements of this gene in the blast cells from a group of 50 patients with T-ALL were studied. These leukemias did not harbor the t(1;14)(p34;q11) translocation. Surprisingly, 13 (26%) of these leukemias contained rearrangements at this locus, all of which were identical at the level of Southern hybridization analysis (U.S. application Ser. No. 07/590,408, filed Sep. 28, 1990, now abandoned; Brown, L., et al. (1990) "Site-specific recombination of the tal-1 gene is a common occurrence in human T cell leukemia," *EMBO J.* 9:3343–3351). Detailed analysis revealed a site-specific of approximately 90 kb deletion on chromosome 1, one end of which lies about 1 kb from the clustered translocation breakpoints in the t(1;14)(p34;q11) cases. As demonstrated by nucleotide sequence analysis, the deletions are all remarkably site-specific, differing at their ends by only a few bases from one leukemia to another. These deletions were not found in remission peripheral blood leukocytes and therefore appear to be leukemia-specific. Thus, site-specific rearrangements at the tal-1 locus characterize nearly 30% of T-ALLs: about 3% are due to translocation (tal$^t$ alleles), while 26% result from an interstitial deletion which is too small to be detected cytogenetically (tal$^d$ alleles).

These rearrangements provide the opportunity to develop sensitive clonal assays for the relevant leukemias. In this invention, it is described assays which can detect 10 rearranged tal-1 cells in a background of $10^6$ normal cells. Moreover, a modification of the assay is presented which quantitates tal$^d$ alleles.

It is, therefore, desirable to have a sensitive assay, using a specific marker, for detecting and monitoring minimal residual leukemia cells in patients under treatment to develop strategies for the prevention of the recurrence of the disease.

SUMMARY OF THE INVENTION

Accordingly, an object of the present invention is to provide a novel, sensitive and specific assay method for detecting minimal residual tumor, such as T-ALL, cells in patients.

Another object of the present invention is to provide a specific oligonucleotide probe to detect and monitor residual leukemic cells in the blood, bone marrow and other body fluids from patients.

Still another object of the present invention is to provide a novel assay method to monitor the number of leukemia cells persisting in a patient during the prolonged treatment of ALL, in particular T-ALL.

Yet another object of the present invention is to provide a sensitive diagnostic test to select the best therapy for each individual leukemic patient through an understanding of how the tumor responds to each phase of treatment.

Still another object of the present invention is to provide a sensitive method to detect the presence of residual tumor cells in a patient without interference from normal cells.

Another object of the present invention is to exploit both immune receptor gene and oncogene rearrangements as clonal markers of tumor populations in a patient.

Another object of the present invention is to provide a method and composition for the quantitation of minimal residual hematopoietic tumor cells in a patient in remission.

Still another object of the present invention is to detect unique DNA rearrangements by sensitive polymerase chain reaction methodology to provide clonal assays for ALL.

Yet another object of the present invention is to provide a test kit for detecting and monitoring of hematopoietic tumor cells in a patient.

Still another object of the present invention is to provide a test kit for quantitating minimal residual hematopoietic tumor cells in remission cells of a patient.

Briefly, it is disclosed a method for monitoring the presence of residual hematopoietic tumor cells in remission cells of a patient, the method comprising the steps of: detecting an alteration of tal-1 locus on chromosome 1 in a DNA extract isolated from the patient; and confirming the presence of the residual hematopoietic tumor cells in the remission cells of the patient based upon detection of the alteration of the patient's chromosome 1.

Additional objects, advantages and novel features of the invention will be set forth in part in the description which follows, and in part will become apparent to those skilled in the art of examination of the following, or may be learned by the practice of the invention.

BRIEF DESCRIPTION OF THE DRAWINGS

Abbreviations used herein are: PCR, polymerase chain reaction; TdT, terminal deoxynucleotidyl transferase; TCR, T cell receptor. Other abbreviations used herein are explained in detail in the Description of the Invention.

DESCRIPTION OF THE INVENTION

Figure 1A:
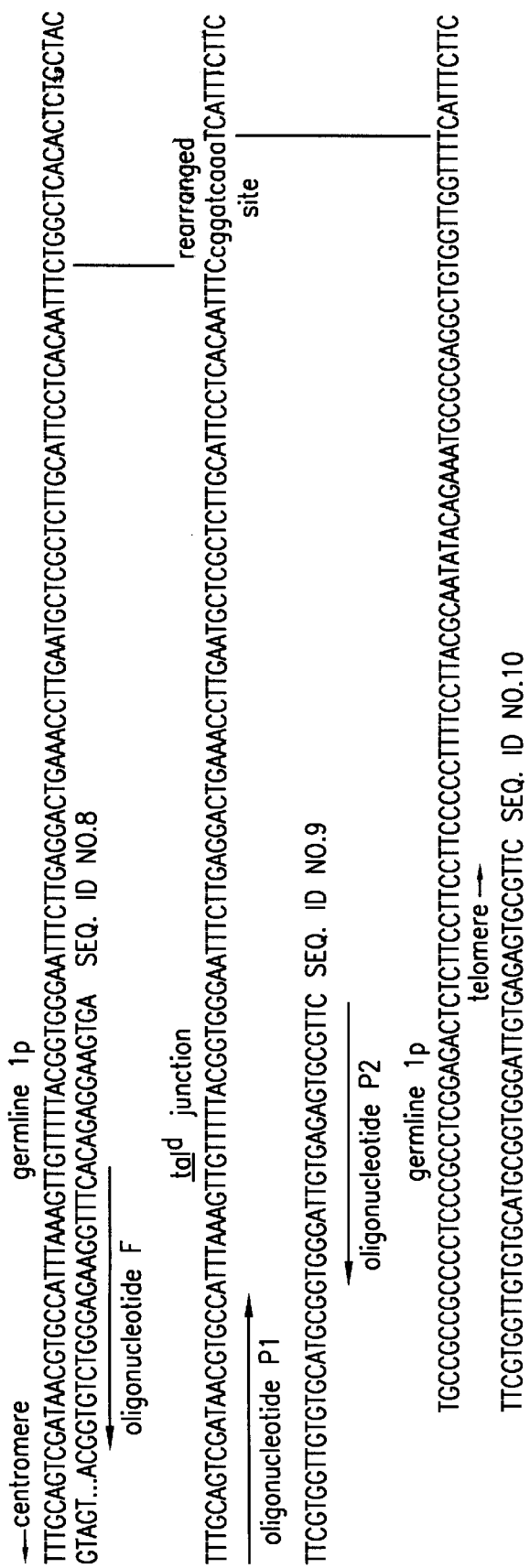
FIG. 1 (Parts A–B). (A) Sequence of the deleted tal-1 (tal$^d$) allele [SEQ ID NO.8] derived from the cultured T-ALL cell line RPMI 8402. The germline sequences of the centromeric (top line [SEQ ID NO.8]) and telomeric (bottom line [SEQ ID NO.10]) sides of the rearrangement are aligned with the tal$^d$ allele (middle line [SEQ ID NO.9]). About 90 kb of the normal sequence is deleted due to the rearrangement (Copending U.S. application Ser. No. 07/590,408, filed Sep. 28, 1990; Brown, L., et al. (1990) "Site-specific recombination of the tal-1 gene is a common occurrence in human T cell leukemia," *EMBO J.* 9:3343–3351). The distal end of this deletion lies in the first intron of the tal-1 gene. Junctional nucleotides not found in the germline sequences are in lower case letters [SEQ ID NO.9]. Oligonucleotides P1 and P2 are used to amplify tal$^d$ alleles. Oligonucleotides P1 and F amplify a 251 bp fragment on the 5' (centromeric) side of normal tal-1 alleles and serve as control primers in PCR assays. Oligonucleotide H is used to detect amplified tal$^d$ alleles in hybridization assays. Dots ( . . . ) in the top line signify nucleotides omitted from the figure. (B) tal$^d$ alleles [SEQ ID NOS.1–7] from 5 T-ALLs, including 3 patients currently in remission (L14 [SEQ ID NO.4], L54 [SEQ ID NO.5], L81 [SEQ ID NO.6]) and 2 cell lines (RPMI 8402 and MOLT 16). As in (A), the tal$^d$ sequences are aligned with germline centromeric (top line [SEQ ID NO.1]) and telomeric (bottom line [SEQ ID NO.7]) sequences, and non-germline nucleotides are shown in lower case letters. The sizes of fragments amplified with oligonucleotides P1 and P2 are shown at the right.

In accordance with the subject invention, novel methods and compositions are provided for the detection, monitoring and quantitation of residual tumor cells in a patient undergoing treatment.

Chromosomal rearrangements or alteration can be of deletion or translocation type. Briefly, the detection of chromosomal rearrangements by PCR amplification and hybridization is as follows: DNA was first extracted from a body tissue, such as white blood cells or bone marrow, of a patient in remission. The DNA was then added to a polymerase chain reaction mixture which contained a first and a second oligonucleotide probe, each of which was substantially concordant with regions of chromosome 1, and which regions spanned the site of rearrangements in the tal-1 gene. After a number of amplification cycles, the products were separated by electrophoresis and visualized by staining. The separated products were further analyzed by molecular hybridization with a third oligonucleotide probe which was concordant with a region of chromosome 1, and which region was in between the regions of concordance to the first and the second oligonucleotide probes.

If rearrangements of the tal-1 gene were detected and confirmed in a patient, these rearrangements were quantitated as follows: An "unknown" DNA from the patient was added to different quantities, precisely measured, of a DNA standard which contained the tal-1 rearrangements. The standard was generally derived from T-ALL cells and was chosen to yield an amplified product which would differ in size from the amplified product derived from the "unknown" DNA. After amplification by PCR, the two products were separated by electrophoresis, stained and quantitated by scanning densitometry. The quantity of tal-1 rearrangements in the "unknown" DNA was determined by comparing the yields of products of the "unknown" and of the standard rearrangements. When the yields were equal, the quantity of the two rearranged alleles in the original reaction mixture was equal as well.

Specifically, the quantitating method comprised the steps of: Simultaneously amplifying a certain amount of an unknown DNA, isolated from a patient carrying hematopoietic cells and containing a first original rearranged allele of tal-1, in the presence of a first known amount of a standard DNA to give (1) a first amplified product obtained from the unknown DNA, and (2) a second amplified product obtained from the standard DNA, the standard DNA being characterized as containing a second original rearranged allele of tal-1 and yielding an amplified product which differed in size from an amplified product obtained from the unknown DNA; separating the first amplified product from the second amplified product; quantitating the yields of the first and second amplified products; and repeating all of the above steps using the same amount of the unknown DNA and a plurality of different known amounts of the standard DNA to give (1) different amplified products obtained from the unknown DNA, and (2) different amplified products obtained from the plurality of different known amounts of the standard DNA. The steps were repeated until crossing an equivalent point wherein the yield of an amplified product obtained from the unknown DNA was equal to the yield of an amplified product obtained from the standard DNA, and wherein the equivalent point was an indication that the original, unamplified, rearranged allele of tal-1 of the unknown DNA was equal to an original, unamplified, rearranged allele of tal-1 in a specific standard DNA selected from the plurality of different known amounts of the standard DNA.

Briefly, the t(1;14)(p34;q11) translocation is found in 3% of T-cell acute lymphoblastic leukemias (T-ALL). In this translocation, the breakpoint on chromosome 1 interrupts the tal-1 gene, which potentially encodes a protein with a helix-loop-helix DNA binding motif. A remarkably site-specific deletion interrupts the same gene in an additional 26% of T-ALL. Thus, nearly one-third of these leukemias contain clustered rearrangements of the tal-1 locus which were exploited as markers for residual disease. Four (4) patients with T-ALL were monitored; 3 of the leukemias contained a deleted (tal$^d$) and one a translocated (tal$^t$) tal-1 allele. These alleles were recognized by an amplification/hybridization assay which could detect 10 rearranged tal-1 alleles per $10^6$ copies of the normal genome. Rearranged tal-1 alleles were not identified in normal peripheral blood mononuclear cells, thymocytes or bone marrow cells. Blood and marrow cells were collected from patients from the 4th through 20th month of antileukemic treatment. tal$^d$ alleles were found in the blood of one patient during the 4th month of treatment but not thereafter. Using a quantitative assay to measure the fraction of tal$^d$ alleles in DNA extracts, it was estimated that this month 4 sample contained 150 tal$^d$ copies per $10^6$ genome copies. The patient with t(1;14)(p34;q11) (tal$^t$) leukemia developed a positive assay during the 20th month of treatment. By standard criteria, all 4 patients remain in complete remission 11–20 months into treatment. Thus, genetic lesions at the tal-1 locus provide clonal markers for monitoring minimal residual disease in approximately 30% of patients with T-ALL.

An increasing variety of therapeutic modalities has appeared, including novel doses and schedules of existing drugs, newer agents such as pentostatin (deoxycoformycin), biologic response modifiers such as α-interferon, immunotoxins, and allogeneic or autologous bone marrow transplantation. Because the total pool of patients is relatively small and prognostic stratification is not well-developed, progress in selection of optimal therapy for individual patients has been limited. Accurate detection and quantitation of disease during the intensive post-induction phase of therapy could facilitate selection of the best consolidation/maintenance approach for each individual patient.

It has now been demonstrated in the present invention that a locus (designated tal) on chromosome 1 is altered in the tumor cells of a significant proportion (about 25%) of patients with T cell acute lymphoblastic leukemia (T-ALL). The tal-1 locus alterations on chromosome 1 can be readily detected by Southern hybridization analysis or by the polymerase chain reaction. The uses of this invention are four-fold: First, the tal-1 locus alterations on chromosome 1 can be used to facilitate the diagnosis of T-ALL. Second, the tal-1 locus alterations on chromosome 1 can be used prognostically to identify T-ALL patients that are likely to suffer a relapse of leukemia after the initial therapy. Third, the tal-1 locus alterations on chromosome 1 can also be used prognostically to track minimal levels of residual disease in T-ALL patients during treatment and during remission. Fourth, different oligonucleotides can be used to quantitate and measure 10 rearranged tal-1 alleles per one million copies of normal genome.

Surprisingly, the rearrangements of tal-1 locus on chromosome 1 observed in different patients are identical, i.e., they all arose from a precise 90 kilobasepair ("kb") deletion that disrupts the coding region of tal-1 in a manner analogous to the t(1;14)(p34;q11) translocation. The extraordinary precision of these deletions (designated tal$^d$) suggests that they are mediated by a site-specific DNA recombinase. Moreover, analysis of the deletion junctions indicates that tal$^d$ rearrangement is engendered by aberrant activity of the same recombinase that controls immunoglobulin and T cell receptor gene assembly.

The term "tal-1 locus" as used herein denotes a region of DNA approximately 200 kb upstream and approximately 200 kb downstream of tal-1 transcription unit. The DNA extract containing chromosome 1 can be isolated from a human tissue such as blood or bone marrow.

Site-specific DNA rearrangements in ALL cells provide clonal markers for the detection of residual disease. These rearrangements are of two sorts: physiologic immune receptor gene rearrangements and pathologic recombinational events such as chromosomal translocations, deletions and insertions. Examples of the former process are TCRδ[1] VDJ segment rearrangements which have been exploited as clonal markers for T-ALL populations (Hansen-Hagge, T. E., et al. (1989) "Detection of minimal residual disease in acute lymphoblastic leukemia by in vitro amplification of rearranged T-cell receptor delta chain sequences," *Blood* 74:1762–1767; Campana, D., et al. (1990) "The detection of residual acute lymphoblastic leukemia cells with immunologic methods and polymerase chain reaction: a comparative study," *Leukemia* 4:609–614). Potential disadvantages of this approach include the requirement for specific probes for each clone, the dominance of new rearrangements during clonal progression and doubts regarding true tumor specificity of the particular rearrangement being monitored. Use of the latter, pathological kinds of rearrangements as clonal markers may overcome these limitations, especially if a site-specific abnormality were found in a large fraction of T-ALLs.

The t(1;14)(p34;q11) translocation is found in only 3% of T-ALL (Carroll, A., et al. (1990) "The t(1;14)(p34;q11) translocation is non-random and restricted to T-cell acute lymphoblastic leukemia," *Blood* 76:1220–1224). The finding of a gene tal-1, encoding a candidate helix-loop-helix DNA binding protein at the site of the breakpoints on chromosome 1p, raised the question whether other, non-translocational rearrangements of this gene might be involved in leukemias of this type. Remarkably, 13 of 50 such leukemias were found to contain nearly identical deletions of approximately 90 kb from the upstream region of this gene (Copending U.S. application Ser. No. 07/590,408, filed Sep. 28, 1990, now abandoned; Brown, L., et al. (1990) "Site-specific recombination of the tal-1 gene is a common occurrence in human T cell leukemia," *EMBO J.* 9:3343–3351). The deletions were not found in remission peripheral blood leukocytes, indicating that tal$^d$ alleles are not germline genetic polymorphisms in these patients (U.S. application Ser. No. 07/590,408, filed Sep. 28, 1990, now abandoned; Brown, L., et al. (1990) "Site-specific recombination of the tal-1 gene is a common occurrence in human T cell leukemia," *EMBO J.* 9:3343–3351). The site of this common rearrangement within the first known intron of the tal-1 locus is approximately 1 kb 5' of a cluster of breakpoints found in the t(1;14)(p34;q11) translocations in T-ALL (Copending U.S. application Ser. No. 07/590,408, filed Sep. 28, 1990, now abandoned; Brown, L., et al. (1990) "Site-specific recombination of the tal-1 gene is a common occurrence in human T cell leukemia," *EMBO J.* 9:3343–3351.) In addition to adding strong circumstantial evidence for a role of these tal-1 rearrangements in the pathogenesis of T-ALL, the remarkably focused nature of the rearrangements provides an opportunity to monitor the leukemic clones with straightforward genomic PCR assays. A single pair of amplimers sufficed for all tal$^d$ alleles, while a few additional pairs should be adequate to detect the tal$^r$ cases. A total of approximately 30% of T-ALLs should thus be amenable to disease monitoring based upon these tal-1 rearrangements.

The success of this approach depends upon the absence of tal-1 rearrangements in normal hematopoietic cells. The site-specific nature of these rearrangements raises the question whether they could play a role in normal T cell development or function. Moreover, aberrant trans-rearrangements involving immune receptor genes have been demonstrated by PCR of normal thymocyte DNA (Tycko, B., et al. (1989) "T cell receptor gene trans-rearrangements: chimeric gamma-delta genes in normal lymphoid tissues," *Science* 245:1242–1246). Since both kinds of tal-1 rearrangements studied herein may originate from misdirected action of the immune receptor recombinase, cell populations containing mature and developing T lymphocytes were examined for evidence of tal$^d$ alleles. Using the amplification/hybridization assay which detects 10 rearranged alleles among $10^6$ cells, no tal$^d$ alleles in normal mature or differentiating hematopoietic tissues were detected. Thus, it is unlikely that rearrangements at the tal-1 locus play any important developmental or functional role in normal T cells. Of practical significance, the low background of these rearrangements in normal hematopoietic cells should not interfere with sensitive and specific detection of the leukemic clones.

In this invention, the suitability of tal-1 gene rearrangements in 4 patients was tested as clonal markers for T-ALL. Of the 3 subjects with tal$^d$ leukemia, evidence of residual disease was found early in remission in one (L54). However, the leukemic tal$^d$ marker was not detected during an ensuing followup period of 7 months. On the other hand, the one patient with t(1;14)(p32;q11) (tal$^r$) disease had a positive PCR assay in his 20th month of treatment which was preceded by a negative assay.

A quantitative assay for tal$^d$ alleles based on the PCR method was developed. The modified assay relies on an internal standard which contains a second tal$^d$ allele distinguishable from the first based on the size of the amplified product. This assay accurately measured 50 to 250 copies of tal$^d$ alleles present in a large excess of normal DNA. Thirty copies of the L54 tal$^d$ allele were found in the L54F1 sample, during the 4th month of treatment.

In accordance with a preferred embodiment invention, a test kit is provided which permits both the detection, or diagnosis, and the monitoring of the hematopoietic tumor cells in a patient. Further, a test kit is provided which permits quantitating the residual hematopoietic tumor cells in remissions cells of a patient.

The detection and monitoring test kit comprises: A first and a second oligonucleotide probe, each of which is substantially concordant with first and second regions of chromosome 1, and which regions span the site of rearrangements of tal-1 gene on chromosome 1 found in a DNA sample isolated from a patient having hematopoietic tumor cells. For better accuracy, the kit may further comprise a third oligonucleotide probe which is substantially concordant with a third region of chromosome 1, which region lies in between the first and second regions, which are sites of concordance with the first and the second oligonucleotide probes. Specifically, the detection and monitoring test kit comprises: A first and a second oligonucleotide probe, both of which are substantially concordant with regions of chromosome 1, and which regions span the site of rearrangements of tal-1 locus on chromosome 1 of a first DNA sample isolated from a patient having T-ALL. These first two oligonucleotide probes shall be used to amplify a product, the presence of which indicates a rearrangement of the tal-1 gene found in patient with T-ALL. The presence of this product will be confirmed by molecular hybridization to a third oligonucleotide probe which is substantially concordant with a chromosome 1 region lying in between the sites of concordance with the first and the second oligonucleotide probes. Further, the test kit may contain a second DNA sample having such rearrangements, and a third DNA sample without having such rearrangements. These second and third DNA samples can be used to confirm that the detection system is working properly.

The quantitating test kit comprises: A first and a second oligonucleotide probe, both of which are substantially concordant with regions of chromosome 1, and which regions span the site of rearrangements of tal-1 gene on chromosome 1 of a first DNA sample isolated from a patient having residual hematopoietic tumor cells; a third oligonucleotide probe which is substantially concordant with a region of chromosome 1, which regions lies in between the sites of concordance with the first and the second oligonucleotide probes; a first series of internal standards of measured dilutions of a second DNA sample from a second T-ALL patient having tal-1 rearrangements, this first series is provided which, after amplification, yields a large-sized product; and a second series of internal standards of measured dilutions of a third DNA sample from a third T-ALL patient, the second series is provided which, after amplification, yields a small-sized product. Each series of internal standards may consist of ten dilutions. For any given quantitation, the standards will be chosen which provides the greater difference in size, after amplification, from the "unknown" sample to be measured.

The methods and compositions of the present invention utilize the following materials and general methods:

Patients and Cells.

Four patients (L14, L23, L54 and L81) with T-ALL were studied. Ages at diagnosis were 10, 7, 9 and 28 years, respectively. The immunophenotype of these leukemias was CD5+CD7+CD19−TdT+[1]. Patients were treated according to Pediatric Oncology Group protocol 8704 (patients L14, L23 and L54) (Amylon, M., et al. (1988) "Treatment of lymphoid malignancies according to immune phenotype: preliminary results in T-cell disease," *Proc. Am. Soc. Clin. Oncol.* 7:225 (Abstr.)) or a minor modification of the Linker regimen for adult ALL (patient L81) (Linker, C. A., et al. (1987) "Improved results of treatment of adult acute lymphoblastic leukemia," *Blood* 69:1242–1248). Normal peripheral blood mononuclear cells were obtained from consenting adults. Small samples of thymus were obtained from children (ages 1–20 months) undergoing cardiac surgery. Vertebral bone marrow was obtained at autopsy from young adult accident victims within 12 hours postmortem. T-ALL cell lines RPMI 8402 (Minowada, J., and G. E. Moore (1975) "T lymphocyte cell lines derived from patients with acute lymphoblastic leukemia," in *Comparative Leukemia Research* 1973: *Leukemogenesis*, Y. Ito and R. Dutcher, editors, University of Tokyo Press, Tokyo. 251–261) and MOLT 16 (Kohno, K., et al. (1986) "Human T-cell leukemia cell lines (MOLT 16 and MOLT 17): production of 112-like factor," *Proc. Jpn. Cancer Assoc.* 45:203 (Abstr.)) were grown in RPMI 1640 medium containing 10% fetal bovine serum. Blood and bone marrow leukocytes were lysed with ammonium chloride and high molecular weight DNA purified by standard methods (Herrmann, B. G., and A-M. Frischauf (1987) "Isolation of genomic DNA," *Methods Enzymol.* 152:180–183).

DNA Amplification.

Figure 2:
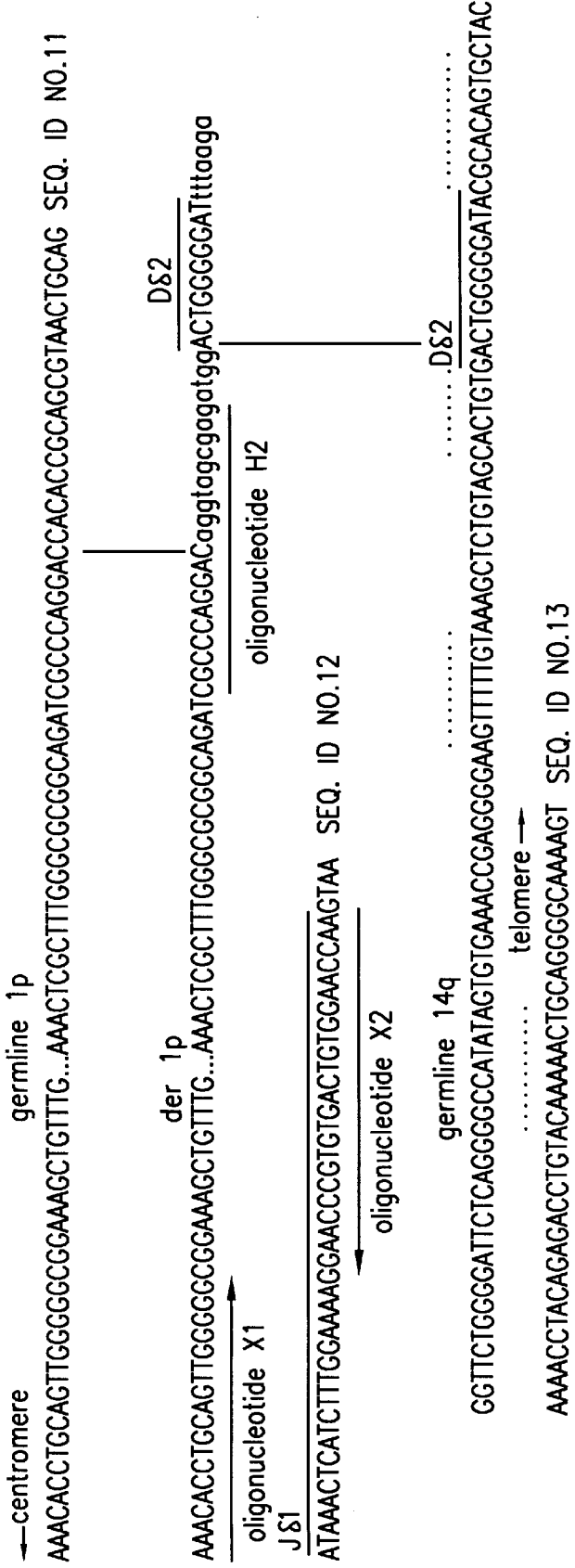
FIG. 2. Sequence of the translocated tal-1 (tal$^r$) allele in T-ALL from patient L-23 [SEQ ID NOS.11–13]. Chromosome 1p (top line [SEQ ID NO.11]) and 14q (bottom line [SEQ ID NO.13]) sequences are aligned with the tal$^r$ allele (middle line [SEQ ID NO.12]). The breakpoint on chromosome 1p is in the first known intron of the tal-1 gene, 2.5 kb 3' of the distal side of the tal$^d$ rearrangements (Chen, Q., et al. (1990) "Coding sequences of the tal-1 gene are disrupted by chromosome translocation in human T cell leukemia," *J. Exp. Med.* 172:1403–1408; U.S. application Ser. No. 07/590,408, filed Sep. 28, 1990, now abandoned; Brown, L., et al. (1990) "Site-specific recombination of the tal-1 gene is a common occurrence in human T cell leukemia," *EMBO J.* 9:3343–3351). The translocation creates a der 1p chromosome, which joins the first exon of the tal-1 gene to a rearranged Dδ2-Jδ1 gene on chromosome 14q11. Non-germline junctional nucleotides are shown in lower case letters. Dδ2 and Jδ1 segments are overlined. Heptamer-nonamer recombination sequences surrounding the germline Dδ2 segment are highlighted with overlying dots. Oligonucleotides X1 and X2 are used to amplify the L23 tal$^r$ allele; oligonucleotide H2 is used to detect this amplified product in a hybridization assay. Dots ( . . . ) in the top and middle lines signify nucleotides omitted from the figure.

Polymerase chain reactions (PCR[1]) were carried out as recommended by the manufacturer (Perkin-Elmer Cetus), except that 1 unit of Perfect Match (Stratagene) was included in each reaction. Oligonucleotide primers P1 and P2, used to detect $tal^d$ alleles, were constructed from the nucleotide sequences on either side of the common deletion (FIG. 1A). Another set of oligonucleotides, X1 and X2, was prepared for the detection of the $tal^r$ translocation in leukemia L23 (FIG. 2). High molecular weight DNA (0.1–10 μg) was added and the corresponding number of genome copies was calculated assuming that $1.5 \times 10^5$ diploid cells contain 1 μg DNA. Amplification was accomplished in a Perkin Elmer Cetus thermal cycler in 60 cycles. The first cycle consisted of 3 min at 94 degrees, 1 min at 61 degrees and 2 min at 72 degrees; in subsequent cycles the melting step lasted 1 min. Control PCR mixtures were run with every experiment and included normal liver or thymus DNA and approximately 1 ng $tal^d$ DNA. Oligonucleotides P1 and F (FIG. 1A) were used to confirm the integrity of the DNA samples; all samples contain at least one normal germline chromosome 1p, which yields a 250 bp fragment upon PCR containing these primers. Standard precautions were taken to avoid contamination of PCR reaction mixtures with PCR products (Kwok, S., and R. Higuchi (1989) "Avoiding false positives with PCR," *Nature* 339:237–238).

Hybridization.

Aliquots of the PCR mixtures were separated on 3% NuSeive/1% SeaKem GTG agarose gels (FMC Bioproducts), denatured, transferred to Hybond-N filters (Amersham) and fixed to the filter by baking. Two kinds of oligonucleotides were used for hybridization. The first, oligonucleotide H, was an 18-mer which detected all $tal^d$ alleles (FIG. 1A). The second were 4 oligonucleotides which detected specific rearrangements in the $tal^d$ leukemias L14, L54 and L81 (FIG. 1B) or the $tal^r$ leukemia L23 (oligonucleotide H2, FIG. 2). End-labeling of oligonucleotides, hybridization and stringent washing was carried out as described (Jonsson, O. G., et al. (1990) "Detection of minimal residual disease in acute lymphoblastic leukemia using immunoglobulin hypervariable region specific oligonucleotide probes," *Blood*, in press).

Oligonucleotide Primers.

Oligonucleotide primers for PCR and hybridization were constructed using an Applied Biosystems Model 380B DNA Synthesizer (Foster City, Calif.). Oligonucleotides F, H, P1 and P2 are shown in FIG. 1A; oligonucleotides X1, X2 and H2 are shown in FIG. 2.

Quantitative PCR Assay for $tal^d$ alleles.

PCR was carried out as described above, except that internal standard DNAs were added to each reaction (Sambrook, J., et al. (1989) "Molecular Cloning: A Laboratory Manual," *Cold Spring Harbor Laboratory Press*, Cold Spring Harbor, N.Y., 14.30–14.33). The standards were chosen to yield an amplified product which differed in size from the target product by approximately 10 bp. Thus, RPMI 8402 DNA was used as a standard in assays for L14 alleles, while MOLT-16 DNA was used in assays for L54 alleles (FIG. 1B). DNA standards were serially diluted into normal liver or thymus DNA (8 μg). The dilutions of standard DNA were added to PCR mixtures containing target DNAs whose $tal^d$ alleles were to be quantitated. The products were separated by electrophoresis through 10% polyacrylamide gels and visualized by staining with ethidium bromide. The original number of target $tal^d$ alleles was estimated by densitometric comparison of staining intensities of the standard and target products. Equal numbers of standard and target alleles present at the start of amplification were shown to generate equal yields of products. Refined estimates of target allele number were obtained by repeating assays in the presence of a narrow range of 2-fold dilutions of standard DNAs.

EXAMPLES

Basis for Detection of tal-1 Gene Rearrangements in T-ALL

The rearrangements of the tal-1 gene exploited in this study are shown in FIGS. 1 and 2. The $tal^d$ alleles are the consequence of an approximately 90 kb deletion which amputates at least one exon of the tal-1 gene on chromosome 1p (U.S. application Ser. No. 07/590,408, filed Sep. 28, 1990, now abandoned; Brown, L., et al. (1990) "Site-specific recombination of the tal-1 gene is a common occurrence in human T cell leukemia," *EMBO J.* 9:3343–3351). The 5' and 3' ends of these deletions are remarkably clustered within a few bp in all $tal^d$ alleles sequenced so far (U.S. application Ser. No. 07/590,408, filed Sep. 28, 1990, now abandoned; Brown, L., et al. (1990) "Site-specific recombination of the tal-1 gene is a common occurrence in human T cell leukemia," *EMBO J.* 9:3343–3351). For the 5 T-ALLs studied herein, the sequences near these ends are shown in FIG. 1B. Each $tal^d$ allele differs by several nucleotides at the proximal and distal ends of the deletion and in the sequence of the extra non-germline nucleotides which replace the deletion. These features enable the specific detection of these alleles by PCR and hybridization assays, as described above. A similar strategy was used to detect the t(1;14)(p32;q11) ($tal^r$) allele in material from patient L23 (FIG. 2).

Distribution of $tal^d$ alleles.

Using Southern hybridization analysis, the $tal^d$ rearrangement was found in 13 of 50 T-ALL diagnostic blood or bone marrow samples (U.S. application Ser. No. 07/590,408, filed Sep. 28, 1990, now abandoned; Brown, L., et al. (1990) "Site-specific recombination of the tal-1 gene is a common occurrence in human T cell leukemia," *EMBO J.* 9:3343–3351). In the present invention, a perfect correlation between results of the Southern and PCR assays of these 50 leukemias was found.

In order for the $tal^d$ PCR assay to be a useful tool for the detection of minimal residual disease, $tal^d$-bearing cells should not be found in normal hematopoietic tissues. Using the PCR assay, no evidence of such cells in normal peripheral blood mononuclear cells (n=40), thymus (n=5) or bone marrow (n=5) was found. The sensitivity of this assay was 5–10 genome copies (cells) per $10^6$. Therefore, within the limits of detection of this assay, $tal^d$ rearrangements are specific for leukemic cells.

Detection of residual disease in T-ALL.

Figure 3:
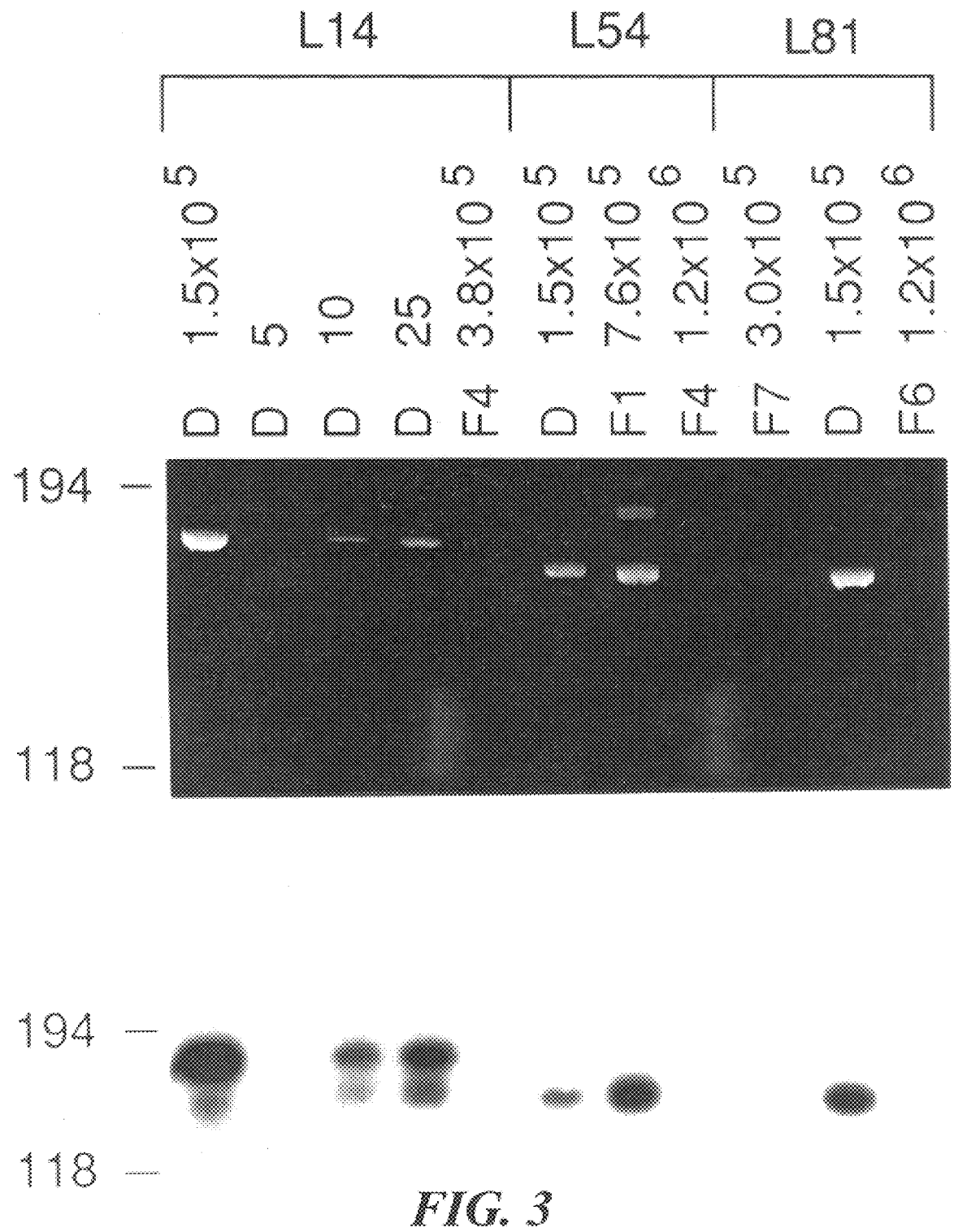
FIG. 3 (Parts A–B). Detection of tal$^d$ alleles by amplification/hybridization assay. PCR mixtures contained oligonucleotides P1 and P2 (FIG. 1A) and high molecular weight DNA derived from blood or bone marrow cells of patients L14, L54 or L81. D indicates diagnostic sample; F samples are followup peripheral blood leukocytes collected during clinical remission (Table 1). The number of genome copies added to PCR mixtures, shown above the lanes, was calculated assuming 1 µg DNA=1.5×10$^5$ genomes. Size markers (bp) are shown by horizontal lines on the left side of the figure. (A) Ethidium bromide-stained 10% polyacrylamide gel of PCR products. (B) Southern hybridization of PCR products with oligonucleotide H (FIG. 1A).

Four patients with T-ALL were studied. Three of these leukemias (L14, L54 and L81) contained the $tal^d$ deletion, while the fourth (L23) had the $tal^r$ translocation. The results of surveillance for $tal^d$ alleles are shown in FIG. 3 and summarized in Table 1. All 4 patients were in complete remission at the time of collection of the samples for assay.

TABLE 1

Rearranged tal-1 alleles in blood and bone marrow samples from T-ALL patients.

| Patient | Sample | Month of Treatment | Detection |
|---------|--------|--------------------|-----------|
| L14*    | D[§]   | 1                  | +         |
|         | F1     | 4                  | −         |
|         | F2     | 17                 | −         |
|         | F3     | 18                 | −         |
|         | F4     | 20                 | −         |
| L54*    | D      | 1                  | +         |
|         | F1     | 4                  | + (150/10$^6$) |
|         | F2     | 5                  | −         |
|         | F3     | 6                  | −         |
|         | F4     | 8                  | −         |
|         | F5     | 9                  | −         |
|         | F6     | 9                  | −         |
|         | F7[§]  | 10                 | −         |
|         | F8     | 11                 | −         |
| LB1*    | D      | 1                  | +         |
|         | F3     | 13                 | −         |
|         | F4     | 14                 | −         |
|         | F6     | 15                 | −         |
| L23■    | D      | 1                  | +         |
|         | F2     | 19                 | −         |

DNA was extracted from diagnostic (D) or followup (F) peripheral blood or bone marrow ([§]) leukocytes and assayed by the amplification/hybridization procedure for tal$^d$ (*) or tal$^r$ (■) alleles. (+), alleles detected; (−), alleles not detected. Both blood and bone marrow from patient L54 were assayed at month 10. tal$^d$ alleles in sample L54F1 were quantitated as described in Methods.

Characteristic bands representing tal$^d$ fragments were amplified in PCRs containing the diagnostic bone marrow samples from each of these 3 patients (FIG. 3, lanes 1, 6 and 10). These bands differ slightly in size, as predicted from the sequences of the corresponding tal$^d$ alleles (FIG. 1B). Dilution experiments demonstrated a sensitivity of detection of 10 copies per 10$^6$ (FIGS. 3A and B, lanes 2–4). tal$^d$ alleles were not detected in blood or bone marrow samples drawn from patients L14 and L81 between the 4th and 20th month of treatment (Table 1). Examples of these negative assays are shown in FIG. 3, lanes 5 and 11. By contrast, tal$^d$ alleles were detected in a blood sample drawn from patient L54 during the 4th month of therapy (FIG. 3, lane 7). However, specimens collected from patient L54 from the 5th through the 11th month of treatment were negative (Table 1).

Figure 4:
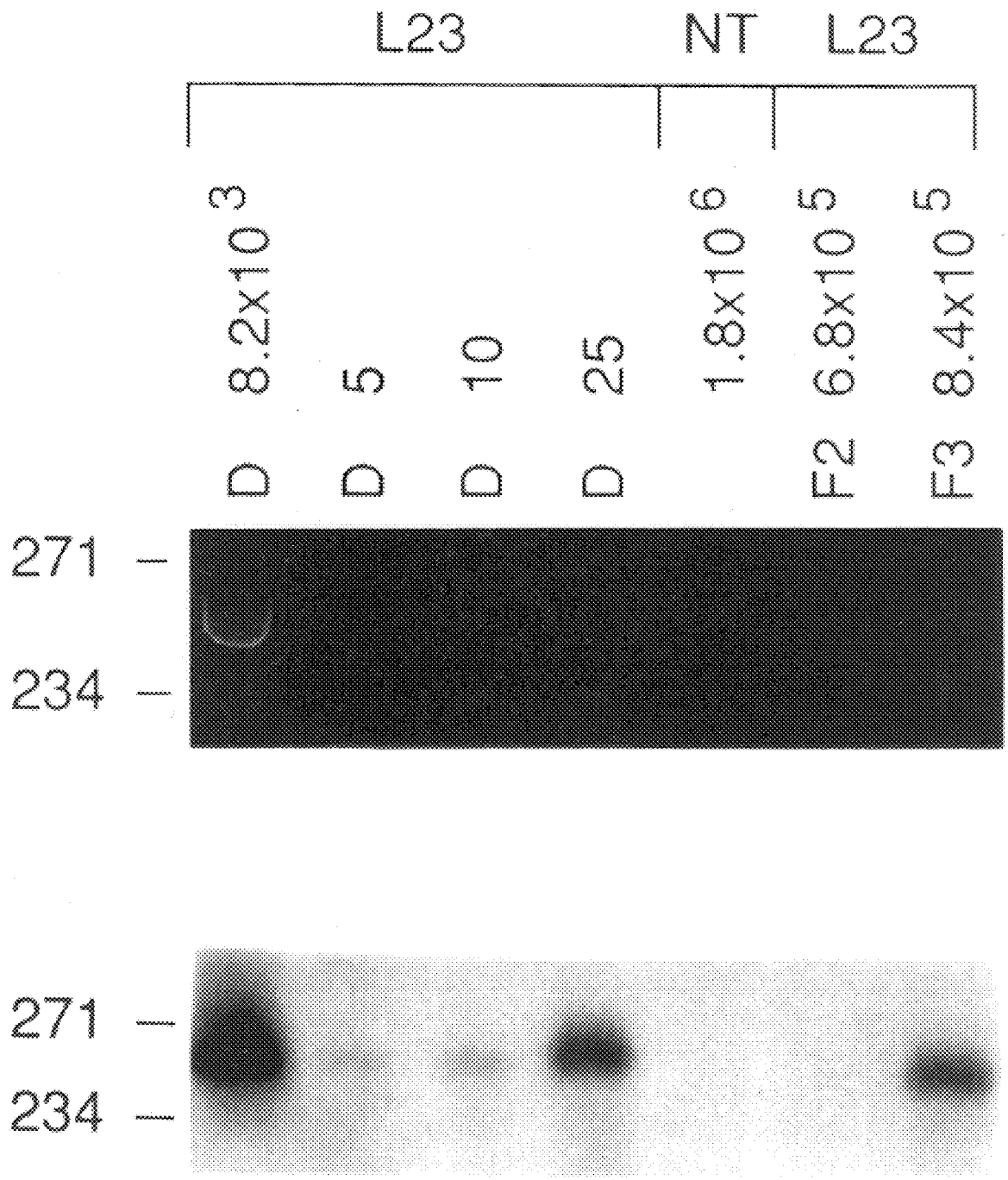
FIG. 4 (Parts A–B). Detection of tal$^r$ alleles by amplification/hybridization assay. PCR mixtures contained oligonucleotides X1 and X2 (FIG. 2) and high molecular weight DNA derived from blood or bone marrow cells of patient L23. D indicates diagnostic sample; F samples are followup peripheral blood leukocytes collected during clinical remission (Table 1). NT indicates normal thymus DNA. The number of genome copies added to PCR mixtures, shown above the lanes, was calculated assuming 1 µg DNA=1.5×10$^5$ genomes. (A) Ethidium bromide-stained 10% polyacrylamide gel of PCR products. (B) Southern hybridization of PCR products with oligonucleotide H2 (FIG. 2).

Detection of tal$^r$ alleles in material from patient L23 is shown in FIG. 4 and Table 1. The characteristic 251 bp band was seen upon amplification of DNA isolated from the diagnostic marrow sample (lane 1). The sensitivity of detection, 5–10 copies per 10$^6$, was similar to that obtained in the tal$^d$ assay (lanes 2–4). A blood sample drawn in the 19th month of therapy was negative (lane 6). However, one month later the assay was clearly positive (lane 7). Since this patient showed no clinical or hematological signs of relapse at the time the latter sample was collected, this assay result implies the appearance of a minimal tumor burden rather late in the course of treatment of patient L23.

Quantitative assay for tal$^d$ alleles.

Figure 5A:
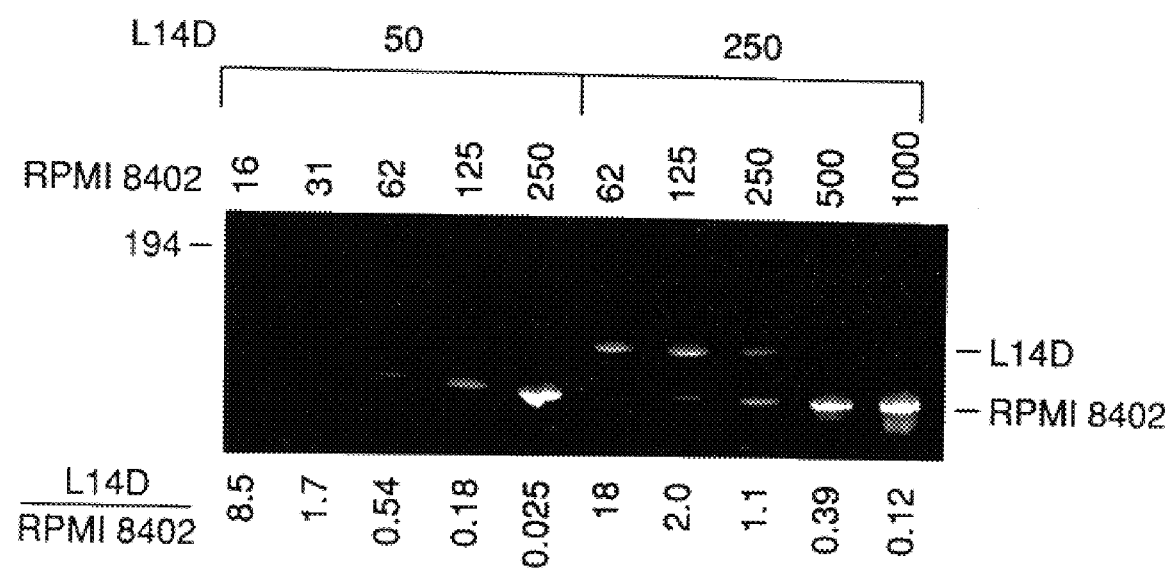
FIG. 5 (Parts A–B). Quantitation of tal$^d$ alleles using an internal standard in PCR assay. (A) Quantitation of L14D tal$^d$ alleles. Varying amounts of RPMI 8402 DNA, shown as genome copies above the lanes, were added to PCR mixtures containing either 50 or 250 genome copies of L14D DNA. The products were analyzed on a 10% polyacrylamide gel and stained with ethidium bromide. The L14D and RPMI 8402 products are marked on the left side of the figure; a size marker (194 bp) is shown on the right. The band intensities were quantitated densitometrically and the ratios of these intensities are shown below the lanes. (B) Quantitation of L54F1 tal$^d$ alleles. Varying amounts of MOLT 16 DNA were added to PCR mixtures containing 1.9×10$^5$ genome copies of L54F1 DNA. The results are displayed as described in (A).
Figure 5B:
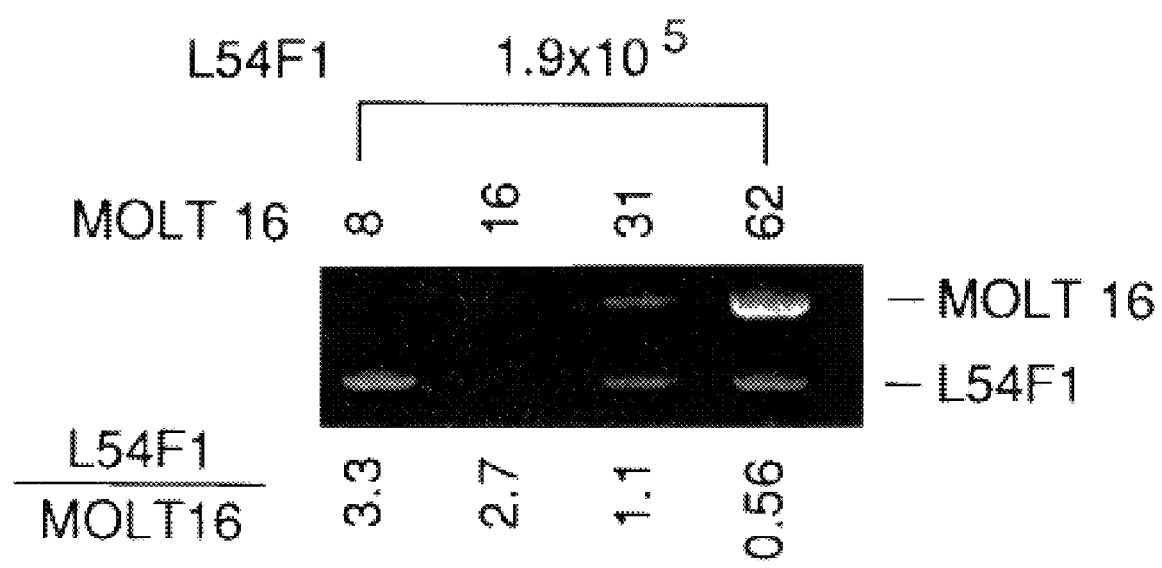

The availability of several tal$^d$ alleles, each of which yielded a PCR product of distinct size, permitted the establishment of a quantitative assay for genomes containing these rearrangements. In this assay, known amounts of a tal$^d$ containing genomic DNA served as internal standards for the measurement of target alleles (Sambrook, J., et al. (1989) "Molecular Cloning:A Laboratory Manual," *Cold Spring Harbor Laboratory Press*, Cold Spring Harbor, N.Y. 14.30–14.33). Standard and target PCR products were distinguished by their different lengths on polyacrylamide gels. The ratio of the yields of the 2 products was estimated by visual inspection and scanning densitometry. Since amplification of these two closely related sequences is equally efficient throughout the PCR, the relative yields depend solely upon the ratio of copies present at the start of the reaction. As shown in FIG. 5A, this assay accurately measured 50 and 250 copies of L14D tal$^d$ alleles diluted into 1.2×10$^6$ normal thymus genome copies. In this case, the RPMI 8402 tal$^d$ allele served as the internal standard for the L14D target allele, the PCR products differing by 11 bp in length (FIG. 1B). To measure the number of tal$^d$ alleles in blood sample L54F1, MOLT 16 DNA was chosen as a standard. Approximately 30 copies of the L54 allele per 1.9×10$^5$ genomes were present at this time point (FIG. 5B). As noted, samples obtained from patient L54 after this time were negative in the amplification/hybridization assay and therefore contained <10 tal$^d$ alleles per sample analyzed (FIG. 3, Table 1).

While the present invention has been particularly described in terms of specific embodiments thereof, it will be understood in view of the present disclosure that numerous variations upon the invention are now enabled to those skilled in the art, which variations yet reside within the scope of the present invention. Accordingly, the invention is to be broadly construed, and limited only by the scope and spirit of the claims now appended hereto. Further, the references cited are hereby incorporated by reference.

We claim:

1. A method for monitoring the presence of residual T-cell acute lymphoblastic leukemia in remission cells of a patient, said method comprising:

detecting a rearrangement of tal-1 locus on chromosome 1 in a DNA extract isolated from said patient, said rearrangement comprising a deletion of about 300 kilobasepair or about 90 kilobasepair; and confirming the presence of said residual hematopoietic tumor cells in said remission cells of said patient based upon detection of said rearrangement of said chromosome 1.

2. The method of claim 1 wherein the step of detecting said rearrangement of said tal-1 locus on chromosome 1 comprises analyzing said DNA extract by Southern hybridization.

3. The method of claim 1 wherein the step of detecting said rearrangement of said chromosome 1 comprises analyzing said DNA extract by polymerase chain reaction.

4. The method of claim 1 further comprising the step of removing a tissue from said patient as a source of said DNA extract.

5. The method of claim 1 wherein said rearrangement comprises a deletion of about 300 kilobasepair disrupting the coding region of the T-cell acute leukemia gene.

6. The method of claim 1 wherein said rearrangements comprise a deletion of about 90 kilobasepair disrupting the coding region of the T-cell acute leukemia gene.

7. The method of claim 1 wherein said rearrangement further comprises chromosomal translocation.

8. A method for monitoring the presence of T-cell acute lymphoblastic leukemia in a patient, said method comprising:

combining sufficiently for product formation and amplification (1) a polymerase chain reaction mixture comprising a first and second oligonucleotide probe, said first probe substantially matching a first region of human chromosome 1 and said second probe substantially matching a second region of said human chromosome 1 and said first and second regions spanning the site of rearrangements in a human tal-1 locus, said rearrangements comprising a deletion of about 300 kilobasepair or about 90 kilobasepair, and (2) a DNA extract from said patient, containing a problematic tal-1 gene on chromosome 1 suspected of being rearranged, wherein detection of a rearrangement of said problematic tal-1 gene on chromosome 1 in said DNA extract from said patient is an indication of the presence of T-cell acute lymphoblastic leukemia in said patient.

9. The method of claim 8 wherein said analyzing step further comprises hybridizing with a third oligonucleotide probe substantially matching with a region in human chromosome 1, which region resides in between said first and second regions.

10. The method of claim 8 wherein said analyzing step comprises analyzing with Southern hybridization.

11. The method of claim 8 further comprising the step of removing a tissue from said patient as a source of said DNA extract.

12. The method of claim 8 wherein said rearrangement further comprises chromosomal translocation.

13. A method for monitoring the presence of hematopoietic tumor cells in a patient, said method comprising:

combining sufficiently for product formation and amplification (1) a polymerase chain reaction mixture comprising a first and a second oligonucleotide probe, said first probe substantially matching a first region of human chromosome 1 and said second probe substantially matching a second region of said human chromosome 1, and said first and second regions spanning the site of rearrangement in a human tal-1 locus, and (2) a DNA extract from said patient, containing a problematic tal-1 gene on chromosome 1 suspected of being rearranged; and analyzing said product formed by said amplification, wherein a detection of a rearrangement of said problematic tal-1 gene of chromosome 1 in said DNA extract from said patient is an indication of the presence of said hematopoietic tumor cells in said patient, said rearrangement comprising a deletion of about 300 kilobasepair or about 90 kilobasepair disrupting the coding region of the T-cell acute leukemia gene.

14. A method for monitoring the presence of hematopoietic tumor cells in a patient, said method comprising:

combining sufficiently for product formation and amplification (1) a polymerase chain reaction mixture comprising a first and a second oligonucleotide probe, said first probe substantially matching a first region of human chromosome 1 and said second probe substantially matching a second region of said human chromosome 1, and said first and second regions spanning the site of rearrangements in a human tal-1 locus, and (2) a DNA extract from said patient, containing a problematic tal-1 gene on chromosome 1 suspected of being rearranged; and analyzing said product formed by said amplification, wherein a detection of a rearrangement of said problematic tal-1 gene on chromosome 1 in said DNA extract from said patient is an indication of the presence of said hematopoietic tumor cells in said patient, said rearrangement comprising a deletion of about 300 kilobasepair or about 90 kilobasepair disrupting the coding region of the T-cell acute leukemia gene.

15. A method for monitoring the presence of residual T-cell acute lymphoblastic leukemia in remission cells of a patient, said method comprising:

combining sufficiently for product formation and amplification (1) a polymerase chain reaction mixture comprising a first and a second oligonucleotide probe, said first probe substantially matching a first region of human chromosome 1 and said second probe substantially matching a second region of said human chromosome 1, and said first and second regions spanning the site or rearrangements in a human tal-1 locus, said rearrangements comprising a deletion of about 300 kilobasepair or about 90 kilobasepair, and (2) a DNA extract from said patient, containing a problematic tal-1 gene on chromosome 1 suspected of being rearranged; and analyzing said product formed by said amplification, wherein a detection of a rearrangement of said problematic tal-1 gene on chromosome 1 in said DNA extract from said patient is an indication of the presence of said residual T-cell acute lymphoblastic leukemia in said remission cells of said patient.

16. The method of claim 15 wherein said analyzing step further comprises hybridizing with a third oligonucleotide probe substantially matching a region in human chromosome 1, which region resides in between said first and second regions.

17. The method of claim 15 wherein said rearrangement further comprises chromosomal translocation.

18. A method for monitoring the presence of residual T-cell acute lymphoblastic leukemia in remission cells of a patient, said method comprising:

combining sufficiently for product formation and amplification (1) a polymerase chain reaction mixture comprising a first and a second oligonucleotide probe, said first probe substantially matching a first region of human chromosome 1 and said second probe substantially matching a second region of said human chromosome 1, and said first and second regions spanning the site of rearrangements in a human tal-1 locus, and (2) a DNA extract from said patient, containing a problematic tal-1 gene on chromosome 1 suspected of being rearranged; and analyzing said product formed by said amplification, wherein a detection of a rearrangement of said problematic tal-1 gene on chromosome 1 in said DNA extract from said patient is an indication of the presence of said residual T-cell acute lymphoblastic leukemia in said remission cells of said patient, said rearrangement comprising a deletion of about 300 kilobasepair or about 90 kilobasepair disrupting the coding region of the T-cell acute leukemia gene.

19. A test kit for the detection of T-cell acute lymphoblastic leukemia in a patient whose chromosome 1 in a DNA extract harbors a rearrangement, said rearrangement comprising a deletion of about 300 kilobasepair or about 90 kilobasepair in a human tal-1 locus, said kit comprising:

a first oligonucleotide probe, said probe substantially matching a first region of said chromosome 1;

a second oligonucleotide probe, said probe substantially matching a second region of said chromosome 1; and said first and second regions spanning the site of said rearrangement in said chromosome 1 of said DNA extract isolated from said patient.

20. A test kit of claim 19 further comprising a third oligonucleotide probe, said probe substantially matching a third region of said chromosome 1, said third region lying in between said first and second regions.

21. The test kit of claim 19 further comprising two additional DNA samples, one of which harbors a known rearrangement in chromosome 1 and the other one harbors no rearrangement in chromosome 1.

22. The test kit of claim 20 wherein:

said first oligonucleotide probe comprises TTTGCAGTCGATAACGTGCC (Seq. No. 14);

said second oligonucleotide probe comprises GAACGCACTCTCACAATCCC (Seq. No. 15);

said third oligonucleotide probe comprises GAAACCTTGAATGCTCGC (Seq. No. 16).

23. The test kit of claim 19 wherein said rearrangement further comprises chromosomal translocation.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 44 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Human
                (B) STRAIN: N/A
                (C) INDIVIDUAL ISOLATE: N/A
                (D) DEVELOPMENTAL STAGE: N/A
                (E) HAPLOTYPE: N/A
                (F) TISSUE TYPE: N/A
                (G) CELL TYPE: N/A
                (H) CELL LINE: N/A (vii) IMMEDIATE SOURCE:
                (A) LIBRARY: N/A
                (B) CLONE: N/A (viii) POSITION IN GENOME:
                (A) CHROMOSOME/SEGMENT: 1p
                (B) MAP POSITION: 1p32-34
                (C) UNITS: 1p (xi) SEQUENCE DESCRIPTION: SEQ ID NO:1:

CATTCCTCAC AATTTCTGGC TCACACTCTG CTACGTAGTA AGGG                        44

(2) INFORMATION FOR SEQ ID NO:2:

(i) SEQUENCE CHARACTERISTICS:
                (A) LENGTH: 35 base pairs
                (B) TYPE: nucleic acid
                (C) STRANDEDNESS: double
                (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Human
                (B) STRAIN: N/A
                (C) INDIVIDUAL ISOLATE: N/A
                (D) DEVELOPMENTAL STAGE: Somatic
                (E) HAPLOTYPE: N/A
                (F) TISSUE TYPE: Lymphoid
                (G) CELL TYPE: Leukemia Cells
                (H) CELL LINE: RPMI8402

(vii) IMMEDIATE SOURCE:
                (A) LIBRARY: N/A
                (B) CLONE: N/A (viii) POSITION IN GENOME:
                (A) CHROMOSOME/SEGMENT: 1p
                (B) MAP POSITION: 1p32-34
                (C) UNITS: 1p (xi) SEQUENCE DESCRIPTION: SEQ ID NO:2:

CATTCCTCAC AATTTCCGGA TCAAATCATT TCTTC                                 35

(2) INFORMATION FOR SEQ ID NO:3:

(i) SEQUENCE CHARACTERISTICS:
                (A) LENGTH: 49 base pairs
                (B) TYPE: nucleic acid
                (C) STRANDEDNESS: double
                (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Human

```
           (B) STRAIN: N/A
           (C) INDIVIDUAL ISOLATE: N/A
           (D) DEVELOPMENTAL STAGE: Somatic
           (E) HAPLOTYPE: N/A
           (F) TISSUE TYPE: Lymphoid
           (G) CELL TYPE: Leukemia Cells
           (H) CELL LINE: Molt-16

(vii) IMMEDIATE SOURCE:
           (A) LIBRARY: N/A
           (B) CLONE: N/A (viii) POSITION IN GENOME:
           (A) CHROMOSOME/SEGMENT: 1p
           (B) MAP POSITION: 1p32-34
           (C) UNITS: bp (xi) SEQUENCE DESCRIPTION: SEQ ID NO:3:

CATTCCTCAC AATTTCTGGC TCTATTAGGG GTTCGGTTTT CATTTCTTC            49

(2) INFORMATION FOR SEQ ID NO:4:

(i) SEQUENCE CHARACTERISTICS:
           (A) LENGTH: 46 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
           (A) ORGANISM: Human
           (B) STRAIN: N/A
           (C) INDIVIDUAL ISOLATE: N/A
           (D) DEVELOPMENTAL STAGE: Somatic
           (E) HAPLOTYPE: N/A
           (F) TISSUE TYPE: Lymphoid
           (G) CELL TYPE: Leukemia Cells
           (H) CELL LINE: L14

(vii) IMMEDIATE SOURCE:
           (A) LIBRARY: N/A
           (B) CLONE: N/A (viii) POSITION IN GENOME:
           (A) CHROMOSOME/SEGMENT: 1p
           (B) MAP POSITION: 1p32-34
           (C) UNITS: bp (xi) SEQUENCE DESCRIPTION: SEQ ID NO:4:

CATTCCTCAC AATTTCTGGG AAACGACTTT TGGTTTTCAT TTCTTC               46

(2) INFORMATION FOR SEQ ID NO:5:

(i) SEQUENCE CHARACTERISTICS:
           (A) LENGTH: 38 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
           (A) ORGANISM: Human
           (B) STRAIN: N/A
           (C) INDIVIDUAL ISOLATE: N/A
           (D) DEVELOPMENTAL STAGE: Somatic
           (E) HAPLOTYPE: N/A
```

```
            (F) TISSUE TYPE: Lymphoid
            (G) CELL TYPE: Leukemia Cells
            (H) CELL LINE: L54

(vii) IMMEDIATE SOURCE:
            (A) LIBRARY: N/A
            (B) CLONE: N/A (viii) POSITION IN GENOME:
            (A) CHROMOSOME/SEGMENT: 1p
            (B) MAP POSITION: 1p32-34
            (C) UNITS: bp (xi) SEQUENCE DESCRIPTION: SEQ ID NO:5:

CATTCCTCAC AATTTCTGGC GTTGGTTTTC ATTTCTTC                              38

(2) INFORMATION FOR SEQ ID NO:6:

(i) SEQUENCE CHARACTERISTICS:
            (A) LENGTH: 35 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Human
            (B) STRAIN: N/A
            (C) INDIVIDUAL ISOLATE: N/A
            (D) DEVELOPMENTAL STAGE: Somatic
            (E) HAPLOTYPE: N/A
            (F) TISSUE TYPE: Lymphoid
            (G) CELL TYPE: Leukemia Cells
            (H) CELL LINE: L81

(vii) IMMEDIATE SOURCE:
            (A) LIBRARY: N/A
            (B) CLONE: N/A (viii) POSITION IN GENOME:
            (A) CHROMOSOME/SEGMENT: 1p
            (B) MAP POSITION: 1p32-34
            (C) UNITS: bp (xi) SEQUENCE DESCRIPTION: SEQ ID NO:6:

CATTCCTCAC AATTTCTGGG GGTTTTCATT TCTTC                                 35

(2) INFORMATION FOR SEQ ID NO:7:

(i) SEQUENCE CHARACTERISTICS:
            (A) LENGTH: 35 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Human
            (B) STRAIN: N/A
            (C) INDIVIDUAL ISOLATE: N/A
            (D) DEVELOPMENTAL STAGE: N/A
            (E) HAPLOTYPE: N/A
            (F) TISSUE TYPE: N/A
            (G) CELL TYPE: N/A
            (H) CELL LINE: N/A
```

(vii) IMMEDIATE SOURCE:
    (A) LIBRARY: N/A
    (B) CLONE: N/A (viii) POSITION IN GENOME:
    (A) CHROMOSOME/SEGMENT: 1p
    (B) MAP POSITION: 1p32-34
    (C) UNITS: bp (xi) SEQUENCE DESCRIPTION: SEQ ID NO:7:

AAATGCGCGA GGCTGTGGTT GGTTTTCATT TCTTC                                      35

(2) INFORMATION FOR SEQ ID NO:8:

(i) SEQUENCE CHARACTERISTICS:
        (A) LENGTH: 156 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Human
        (B) STRAIN: N/A
        (C) INDIVIDUAL ISOLATE: N/A
        (D) DEVELOPMENTAL STAGE: Somatic
        (E) HAPLOTYPE: N/A
        (F) TISSUE TYPE: Lymphoid tumor
        (G) CELL TYPE: Leukemia cells
        (H) CELL LINE: RPMI8402

(vii) IMMEDIATE SOURCE:
        (A) LIBRARY: RPMI8402
        (B) CLONE: AA-0.6

(viii) POSITION IN GENOME:
        (A) CHROMOSOME/SEGMENT: 1p
        (B) MAP POSITION: 1p32-34
        (C) UNITS: bp (xi) SEQUENCE DESCRIPTION: SEQ ID NO:8:

TTTCGAGTCG ATAACGTGCC ATTTAAAGTT GTTTTTACGG TGGGAATTTC TTGAGGACTG            60

AAACCTTGAA TGCTCGCTCT TGCATTCCTC ACAATTTCTG GCTCACACTC TGCTACGTAG           120

TACGGTGTCT GGGAGAAGGT TTCACAGAGG AAGTGA                                    156

(2) INFORMATION FOR SEQ ID NO:9:

(i) SEQUENCE CHARACTERISTICS:
        (A) LENGTH: 159 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
        (A) ORGANISM: Human
        (B) STRAIN: N/A
        (C) INDIVIDUAL ISOLATE: N/A
        (D) DEVELOPMENTAL STAGE: Somatic
        (E) HAPLOTYPE: N/A
        (F) TISSUE TYPE: Lymphoid tumor
        (G) CELL TYPE: Leukemia cells
        (H) CELL LINE: RPMI8402

(vii) IMMEDIATE SOURCE:
             (A) LIBRARY: RPMI8402
             (B) CLONE: BLI (viii) POSITION IN GENOME:
             (A) CHROMOSOME/SEGMENT: 1p
             (B) MAP POSITION: 1p32-34
             (C) UNITS: bp (xi) SEQUENCE DESCRIPTION: SEQ ID NO:9:

TTTGCAGTCG ATAACGTGCC ATTTAAAGTT GTTTTTACGG TGGGAATTTC TTGAGGACTG      60

AAACCTTGAA TGCTCGCTCT TGCATTCCTC ACAATTTCCG GATCAAATCA TTTCTTCTTC     120

GTGGTTGTGT GCATGCGGTG GGATTGTGAG AGTGCGTTC                            159

(2) INFORMATION FOR SEQ ID NO:10:

(i) SEQUENCE CHARACTERISTICS:
            (A) LENGTH: 144 base pairs
            (B) TYPE: nucleic acid
            (C) STRANDEDNESS: double
            (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
            (A) ORGANISM: Human
            (B) STRAIN: N/A
            (C) INDIVIDUAL ISOLATE: N/A
            (D) DEVELOPMENTAL STAGE: Somatic
            (E) HAPLOTYPE: N/A
            (F) TISSUE TYPE: Lymphoid tumor
            (G) CELL TYPE: Leukemia cells
            (H) CELL LINE: Patient No. 4

(vii) IMMEDIATE SOURCE:
            (A) LIBRARY: B
            (B) CLONE: B2EE-2.0

(viii) POSITION IN GENOME:
            (A) CHROMOSOME/SEGMENT: 1p
            (B) MAP POSITION: 1p32-34
            (C) UNITS: bp (xi) SEQUENCE DESCRIPTION: SEQ ID NO:10:

TGCCGCCGCC CCTCCCGCCT CGGAGACTCT CTTCCTTCCT TCCCCCTTTT CCTTACGCAA      60

TATACAGAAA TGCGCGAGGC TGTGGTTGGT TTTCATTTCT TCTTCGTGGT TGTTGTCATG     120

CGGTGGGATT GTGAGAGTGC GTTC                                           144

(2) INFORMATION FOR SEQ ID NO:11:

(i) SEQUENCE CHARACTERISTICS:
            (A) LENGTH: 88 base pairs
            (B) TYPE: nucleic acid
            (C) STRANDEDNESS: double
            (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
            (A) ORGANISM: Human
            (B) STRAIN: N/A
            (C) INDIVIDUAL ISOLATE: N/A
            (D) DEVELOPMENTAL STAGE: Somatic
            (E) HAPLOTYPE: N/A

```
                (F) TISSUE TYPE: Lymphoid tumor
                (G) CELL TYPE: Leukemia cells
                (H) CELL LINE: SUP-T3

(vii) IMMEDIATE SOURCE:
                (A) LIBRARY: SU
                (B) CLONE: SU2

(viii) POSITION IN GENOME:
                (A) CHROMOSOME/SEGMENT: 1p
                (B) MAP POSITION: 1p32-34
                (C) UNITS: bp (xi) SEQUENCE DESCRIPTION: SEQ ID NO:11:

AAACACCTGC AGTTGGGGGC GGAAAGCTGT TTGAAACTCG CTTTGGGCGC GGCAGATCGC        60

CCAGGACCAC ACCGCAGCGT AACTGCAG                                          88

(2) INFORMATION FOR SEQ ID NO:12:

(i) SEQUENCE CHARACTERISTICS:
                (A) LENGTH: 147 base pairs
                (B) TYPE: nucleic acid
                (C) STRANDEDNESS: double
                (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
                (A) ORGANISM: Human
                (B) STRAIN: N/A
                (C) INDIVIDUAL ISOLATE: N/A
                (D) DEVELOPMENTAL STAGE: Somatic
                (E) HAPLOTYPE: N/A
                (F) TISSUE TYPE: Lymphoid tumor
                (G) CELL TYPE: Leukemia cells
                (H) CELL LINE: Patient L23

(vii) IMMEDIATE SOURCE:
                (A) LIBRARY: N/A
                (B) CLONE: PCR-L23

(viii) POSITION IN GENOME:
                (A) CHROMOSOME/SEGMENT: t(1;14) Translocation
                (B) MAP POSITION: 1p32-34 and 14q11
                (C) UNITS: bp (xi) SEQUENCE DESCRIPTION: SEQ ID NO:12:

AAACACCTGC AGTTGGGGGC GGAAAGCTGT TTGAAACTCG CTTTGGGCGC GGCAGATCGC        60

CCAGGACAGG TAGCGAGATG GACTGGGGGA TTTTAAGAAT AAACTCATCT TTGGAAAAGG      120

AACCCGTGTG ACTGTGGAAC CAAGTAA                                         147

(2) INFORMATION FOR SEQ ID NO:13:

(i) SEQUENCE CHARACTERISTICS:
                (A) LENGTH: 139 base pairs
                (B) TYPE: nucleic acid
                (C) STRANDEDNESS: double
                (D) TOPOLOGY: Not Relevant (ii) MOLECULE TYPE: DNA (genomic)

(iii) HYPOTHETICAL: NO (iv) ANTI-SENSE: NO (vi) ORIGINAL SOURCE:
                (A) ORGANISM: Human
                (B) STRAIN: N/A
                (C) INDIVIDUAL ISOLATE: N/A
```

(D) DEVELOPMENTAL STAGE: Somatic
              (E) HAPLOTYPE: N/A
              (F) TISSUE TYPE: Lymphoid tumor
              (G) CELL TYPE: Leukemia cells
              (H) CELL LINE: RPMI8402

(vii) IMMEDIATE SOURCE:
              (A) LIBRARY: RPMI8402
              (B) CLONE: R28

(viii) POSITION IN GENOME:
              (A) CHROMOSOME/SEGMENT: 14q
              (B) MAP POSITION: 14q11
              (C) UNITS: bp (xi) SEQUENCE DESCRIPTION: SEQ ID NO:13:

GGTTCTGGGG ATTCTCAGGG GCCATATAGT GTGAAACCGA GGGGAAGTTT TTGTAAAGCT      60

CTGTAGCACT GTGACTGGGG GATACGCACA GTGCTACAAA ACCTACAGAG ACCTGTACAA     120

AAACTGCAGG GGCAAAAGT                                                  139

(2) INFORMATION FOR SEQ ID NO:14:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Human
              (B) STRAIN: N/A
              (C) INDIVIDUAL ISOLATE: N/A
              (D) DEVELOPMENTAL STAGE: Somatic
              (E) HAPLOTYPE: N/A
              (F) TISSUE TYPE: Lymphoid tumor
              (G) CELL TYPE: Leukemia cells
              (H) CELL LINE: RPMI8402

(vii) IMMEDIATE SOURCE:
              (A) LIBRARY: RPMI8402
              (B) CLONE: AA-0.6

(viii) POSITION IN GENOME:
              (A) CHROMOSOME/SEGMENT: 1p
              (B) MAP POSITION: 1p32-34
              (C) UNITS: bp (xi) SEQUENCE DESCRIPTION: SEQ ID NO:14:

TTTGCAGCCG ATAACGTGCC                                                  20

(2) INFORMATION FOR SEQ ID NO:15:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (vi) ORIGINAL SOURCE:
              (A) ORGANISM: Human
              (B) STRAIN: N/A
              (C) INDIVIDUAL ISOLATE: N/A

```
        (D) DEVELOPMENTAL STAGE: Somatic
        (E) HAPLOTYPE: N/A
        (F) TISSUE TYPE: Lymphoid tumor
        (G) CELL TYPE: Leukemia cells
        (H) CELL LINE: Patient No. 4

(vii) IMMEDIATE SOURCE:
        (A) LIBRARY: B
        (B) CLONE: B2EE-2.0

(viii) POSITION IN GENOME:
        (A) CHROMOSOME/SEGMENT: 1p
        (B) MAP POSITION: 1p32-34
        (C) UNITS: bp (xi) SEQUENCE DESCRIPTION: SEQ ID NO:15:

GAACGCACTC TCACAATCCC                                                   20

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human
        (B) STRAIN: N/A
        (C) INDIVIDUAL ISOLATE: N/A
        (D) DEVELOPMENTAL STAGE: Somatic
        (E) HAPLOTYPE: N/A
        (F) TISSUE TYPE: Lymphoid tumor
        (G) CELL TYPE: Leukemia cells
        (H) CELL LINE: RPMI8402

(vii) IMMEDIATE SOURCE:
        (A) LIBRARY: RPMI8402
        (B) CLONE: AA-0.6

(viii) POSITION IN GENOME:
        (A) CHROMOSOME/SEGMENT: 1p
        (B) MAP POSITION: 1p32-34
        (C) UNITS: bp (xi) SEQUENCE DESCRIPTION: SEQ ID NO:16:

GAAACCTTGA ATGCTCGC                                                     18
```